(12) United States Patent
Ali

(10) Patent No.: US 8,602,986 B2
(45) Date of Patent: Dec. 10, 2013

(54) SYSTEM AND METHOD FOR DETECTING SIGNAL ARTIFACTS

(75) Inventor: Walid Ali, Chandler, AZ (US)

(73) Assignee: Koninklijke Philips N.V., Eindhoven (NL)

( * ) Notice: Subject to any disclaimer, the term of this patent is extended or adjusted under 35 U.S.C. 154(b) by 1776 days.

(21) Appl. No.: 10/568,173

(22) PCT Filed: Aug. 6, 2004

(86) PCT No.: PCT/IB2004/002629
§ 371 (c)(1),
(2), (4) Date: Feb. 10, 2006

(87) PCT Pub. No.: WO2005/020120
PCT Pub. Date: Mar. 3, 2005

(65) Prior Publication Data
US 2006/0247501 A1    Nov. 2, 2006

Related U.S. Application Data

(60) Provisional application No. 60/496,418, filed on Aug. 20, 2003.

(51) Int. Cl.
*A61B 5/02* (2006.01)
(52) U.S. Cl.
USPC .......................................... 600/301; 600/508
(58) Field of Classification Search
USPC .......... 600/301, 508–509, 513, 515; 382/131; 340/567; 381/66
See application file for complete search history.

(56) References Cited

U.S. PATENT DOCUMENTS

| | | | | |
|---|---|---|---|---|
| 4,746,910 A | * | 5/1988 | Pfister et al. ................... | 340/567 |
| 5,217,021 A | * | 6/1993 | Steinhaus et al. ............. | 600/515 |
| 5,348,008 A | * | 9/1994 | Bornn et al. ................... | 600/301 |
| 5,661,813 A | * | 8/1997 | Shimauchi et al. ............. | 381/66 |
| 5,694,942 A | * | 12/1997 | Escalona ........................ | 600/509 |
| 5,902,249 A | * | 5/1999 | Lyster ........................... | 600/509 |
| 5,921,937 A | * | 7/1999 | Davis et al. ................... | 600/508 |
| 5,944,669 A | * | 8/1999 | Kaib ............................. | 600/512 |
| 6,171,256 B1 | * | 1/2001 | Joo et al. ....................... | 600/508 |
| 6,217,525 B1 | * | 4/2001 | Medema et al. ............... | 600/508 |
| 6,287,328 B1 | * | 9/2001 | Snyder et al. ................. | 600/509 |
| 2002/0016548 A1 | * | 2/2002 | Stadler et al. ................ | 600/509 |
| 2002/0193670 A1 | * | 12/2002 | Garfield et al. ............... | 600/304 |
| 2007/0032705 A1 | * | 2/2007 | Ali ................................. | 600/300 |

FOREIGN PATENT DOCUMENTS

| | | | |
|---|---|---|---|
| WO | WO 2005/036440 | * | 4/2005 |
| WO | WO 2005/036440 A3 | * | 4/2005 |

OTHER PUBLICATIONS

Laguna et al. "Adaptive Filter for Event-Related Bioelectric Signals Using an Impulse Correlated Reference Input: Comparison with Signal Averaging Techniques." IEEE Transactions on Biomedical Engineering. vol. 39, No. 10. Oct. 1992.*

* cited by examiner

*Primary Examiner* — Carl H Layno
*Assistant Examiner* — Luther Behringer

(57) ABSTRACT

A method and system are disclosed that detect signal artifacts in one or more event signals. The system and method may be used with a patient monitoring apparatus that adapts to a patient's condition and distinguishes between clinically significant changes in the patient's state verse clinically insignificant changes.

16 Claims, 3 Drawing Sheets

SYSTEM AND METHOD FOR DETECTING SIGNAL ARTIFACTS

CROSS REFERENCE TO RELATED APPLICATIONS

This application claims the benefit of U.S. provisional application Ser. No. 60/496,418 filed Aug. 20, 2003, which is incorporated herein by reference.

The present invention relates to a system and method for detecting signal artifacts, in particular, to system and a method used with a patient monitoring apparatus that adapts to a patient's condition and distinguishes between clinically-significant changes in the patient's state verse clinically-insignificant changes.

One common problem associated with the use of measurement instruments is erroneous measurements that result from the introduction of an artifact signal into the event signal of interest. Typically, a measurement instrument detects one or more measured signals each comprised of the event signal of interest along with some level of artifact related to one or more non-event signals. The resulting measured signals can become significantly corrupted such that they should not be relied upon as an accurate representation of the event signal. Artifacts that corrupt the event signals can result from mechanical disturbances of sensors, electromagnetic interference, etc. As will be appreciated by those of skill in the art, the nature of the artifact signals will vary depending on the nature of the measuring instrument and the environmental conditions under which the measurements are taken.

One area in which the presence of artifact signals presents a potentially life-threatening problem is in the area of medical diagnostics and instrumentation. The appearance of a non-event signal in a patient monitoring device could result in a clinician making an incorrect decision with respect to a patient's treatment, or, for devices that use algorithms to make decisions, could result in the device itself making an incorrect assessment of the patient's condition.

In conventional patient monitoring systems, alarms are typically generated on crossing a limit or threshold in a signal being monitored, e.g., heart rate. While the threshold method is useful in determining physiological limits of variation of a parameter, it is not always the best method of event detection. The information that the clinician usually wants is the detection of relevant abnormalities or changes in a patient's condition. This is not easily reflected in a value crossing a limit, but rather by the simultaneous evolution of different parameters.

In practice, wide variations in a given parameter can be observed without any major alteration of the physiological function of a patient. Many of these fluctuations cause a false alarm in conventional patient monitoring systems. While the parameter being monitored did cross the limit, the alarm has no clinical significance. In such a case, for example, no major event is related to the worsening of the patient's status. As a result of this, many alarms in conventional patient monitoring systems are usually perceived as unhelpful by medical staff because of the high incidence of false alarms, i.e., alarms with no clinical significance.

As discussed above, conventional alarm techniques generate an alarm signal based on setting a threshold. For every parameter, the trigger of the alarm is set off immediately if its value reaches the limit or in some cases when its value has been beyond the limit for a given time. On the same patient monitoring system, when the values of several parameters are beyond the limit, an audible signal may be triggered on the first parameter that reached the alarm threshold; alternatively there can be a hierarchy of alarms. Generally, in all cases, it is necessary to set the threshold alarm limit.

Conventional patient monitoring systems provide for the setting of an alarm on most physiological data. In some cases, more than 40 alarm sources can be active, e.g., ventilation data, electrocardiogram, arterial pressure and pulse oximetry for a patient undergoing mechanical ventilation. In addition, perfusion pumps, nutrition pumps, automatic syringes and dialysis systems may also generate alarms.

False alarms may have several adverse consequences. A constant stream of false alarms may result in nurses delaying their intervention or trying to recognize life-threatening alarms by sound only. This practice may have severe consequences when the patient's condition is deteriorating.

What is needed is an improved method for detecting the presence and significance of artifact signals that may corrupt an event signal so that false alarms can be minimized.

The present invention is directed to a method and system for detecting signal artifacts, in particular, to system and a method used with a patient monitoring apparatus that adapts to a patient's condition and distinguishes between clinically-significant changes in the patient's state verse clinically-insignificant changes One embodiment of the present invention is directed to a method for detecting a signal artifact in an event signal. The method including the steps of receiving at least two event signals, determining a global correlation for the at least two event signal over a first period of time, determining a local correlation for the at least two event signals over a second period of time which is shorter than the first period of time, determining a deviation between a local correlation vector and a global correlation vector, determining an average deviation from the deviation, and determining whether an artifact was detected in one of the at least two event signals based upon the average deviation.

Another embodiment of the present invention is directed to a device including a controller, a memory coupled to the controller, and an input interface arranged to received at least two event signals.

A more complete understanding of the method and apparatus of the present invention is available by reference to the following detailed description when taken in conjunction with the accompanying drawings wherein.

In the following description, for purposes of explanation rather than limitation, specific details are set forth such as the particular architecture, interfaces, techniques, etc., in order to provide a thorough understanding of the present invention. For purposes of simplicity and clarity, detailed descriptions of well-known devices, circuits, and methods are omitted so as not to obscure the description of the present invention with unnecessary detail.

Figure 1:
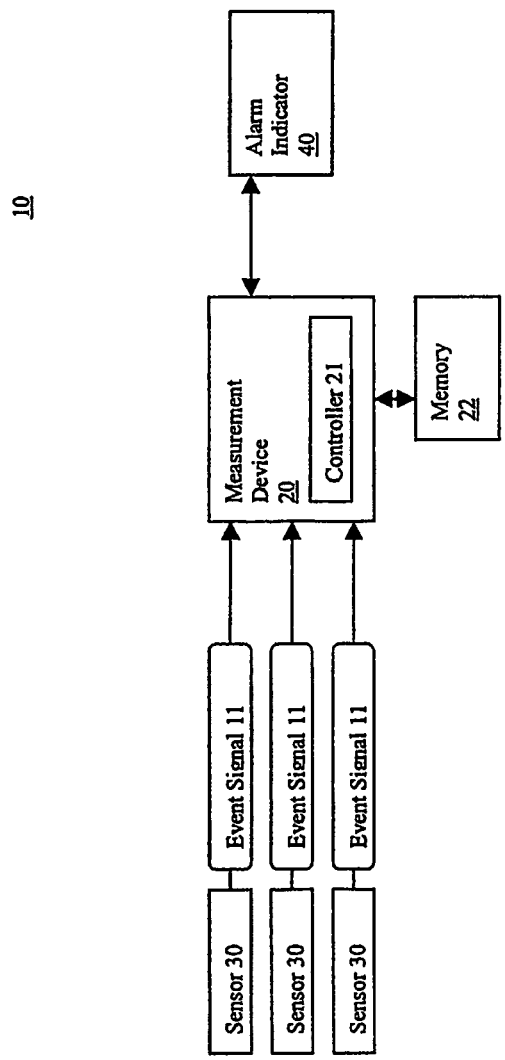
FIG. 1 depicts a diagram of a monitoring system according to an embodiment of the present invention.

FIG. 1 is a block diagram showing a system 10 according to one aspect of the present invention. One or more potentially corrupted event signals 11 are provided to a measurement device 20. The measurement device 20 includes a controller 21. The system 10 may also include a plurality of sensors 30 that obtain the event signals 11 and provide event signals 11 to the measurement system 20.

Several specific implementations of the system 10 are contemplated. For example, in one specific embodiment, the system 10 is a patient monitoring system capable of monitoring a plurality of patient parameters. Patient parameters include, but are not limited to, ECG, EEG, pulse, temperature, or any other biological activity. These patient parameters would be the event signals 11 of interest. In another more specific implementation, the system 10 is a defibrillator capable of measuring an ECG. In that instance, the ECG would be the event signal 11 of interest.

In another implementation, the measurement device 20 is part of a server in a client-servant network, e.g., the Internet.

As will be appreciated by those of skill in the art, the present invention is not limited to medical applications. The artifact detection techniques of the present invention can be used to detect artifact from any measured input signal source. For example, equipment that is used to measure ocean temperature, seismic activity, etc. can be set-up so that additional input signals are provided for signal processing and correlation with the signal of interest in order to determine whether the signal of interest has been corrupted with artifact. In addition, aspects of the present invention can be applied to systems that measure multiple event signals, wherein each event signal would employ this artifact detection method.

For purposes of illustration, an artifact detection technique in accordance with one embodiment of the present invention is described below in conjunction with patient monitoring equipment.

In this embodiment, a plurality of patient event signals 11 ($s_1, s_2, s_3, \ldots, s_n$) are monitored. In this embodiment, the measurement device 20 is a patent monitoring system such as those used in an intensive care unit of a hospital. As one or more of the sensors 30 are connected to a patient, the event signals 11 start flowing into the measurement device 20. In this embodiment, the measurement device includes a memory 21 for recording the input event signals 11.

Figure 2:
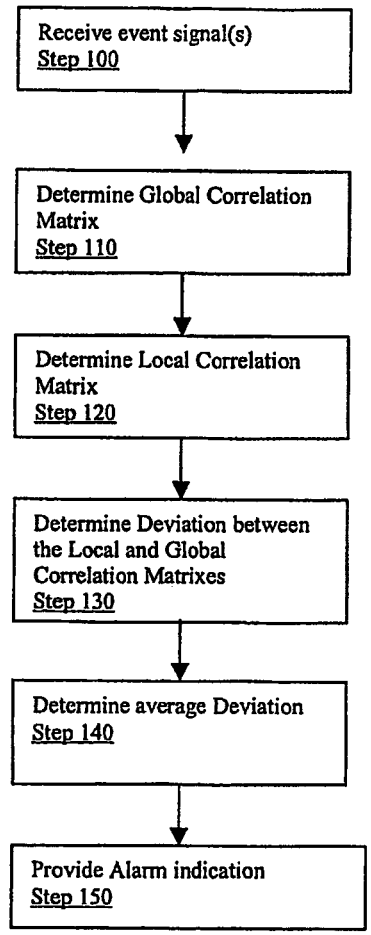
FIG. 2 is a flow chart illustrating a method in accordance with one aspect of the present invention.

For each of the plurality of patient event signals 11 an indicator for the presence of artifacts in each is needed. FIG. 2 is a flow chart showing the steps of obtaining such an indicator. In a preferred embodiment, the steps shown in FIG. 2 are implemented by computer readable code executed by a data processing apparatus or controller 21. The code may be stored in a memory (e.g., memory 22) within the data processing apparatus or read/downloaded from a memory medium such as a CD-ROM or floppy disk. In other embodiments, hardware circuitry may be used in place of, or in combination with, software instructions.

In step 100, a history of event signals 11 is gathered and/or received. For example, in the patient monitoring system situation, event signals 11 are received for each patient to be monitored. This history may be a few minutes and may expand over a few days. Preferably, this history is at least ten minutes. The history data can be fixed for a specific period of time or be updated at predetermined times, every ten minutes, every hour, etc. For example, in the case of the patient monitoring system, the history for particular patient may be fixed as the first hour the patient is being monitored.

In the case of patient monitoring systems, samples are typically collected at a rate of ~125 samples/second. Other sample rates, however, may also be used. Accordingly, in a matter of few minutes to a few hours of time T, a large number of samples (history) for each of the monitored event signals 11 ($s_1, s_2, s_3, \ldots, s_n$) are collected.

In step 110, a cross correlation, "r", among these recorded event signals 11 is determined. The cross correlation provide an overall correlation matrix, $r_{global}$, as shown in equation (1) below. This overall correlation matrix provides a norm or steady state for a particular patient.

$$r_{Global} = \begin{pmatrix} r_{11} & \cdots & r_{1n} \\ \vdots & & \vdots \\ r_{n1} & \cdots & r_{nn} \end{pmatrix}_{Global} \tag{1}$$

In step 120, a local correlation matrix is calculated over shorter periods of time is calculated. The short-term period of time may be a few seconds to a few minutes (typically 12 seconds). In the present patient monitoring example, a short-term period of 12 seconds yields 1500 samples per signal. This results in a local correlation matrix, as shown in equation (2) below.

$$r_{Local_l} = \begin{pmatrix} r_{11} & \cdots & r_{1n} \\ \vdots & & \vdots \\ r_{n1} & \cdots & r_{nn} \end{pmatrix}_{Local_l} \tag{2}$$

Where the number of these local correlation matrixes equals N $$N = \frac{T \text{ (in seconds)}}{12 \text{ (Number of seconds for local correlation calculation)}} \tag{3}$$

In step 130, the deviation between the local correlation matrix feature vector and the global correlation matrix is determined. This is an indication of the current patient status and its variability.

This difference is defined as $$\vec{D}_i = r_{Global} - r_{Local_l} \tag{4}$$

The root mean square of this deviation vector is an indicator of the absolute value for the deviation between the current status and the global information.

$$D_i = |r_{Global} - r_{Local_l}| \tag{5}$$

In step 140, the average deviation is determined. This is an indicator of the normal/acceptable instantaneous deviation of the patient's recorded information vs. his/her overall recorded history.

$$D_{average} = \frac{1}{N} \sum_{i=1}^{N} D_i \tag{6}$$

When any of the monitored event signals 11 suffer from the presence of an artifact, its local correlation matrix (equation 2) varies largely from the global correlation matrix (equation 1) and the associating deviation (equation 5) varies largely from the average deviation (between local and global correlation matrix as defined in equation 6).

When an alarm is present with a large deviation away from $D_{average}$, this is an indication that the normal correlation pattern has been locally violated and the alarm present is of low credibility and most likely is a false alarm. Generally a large deviation is in the range of 10%. However, the exact range for a "large" deviation can be adjusted in accordance with known fluctuations in particular signals and/or normally observes ranges in such event signals.

In step 150, if the deviation is less than and/or equal to a predetermined threshold range an alarm indication may be provided.

Figure 3:
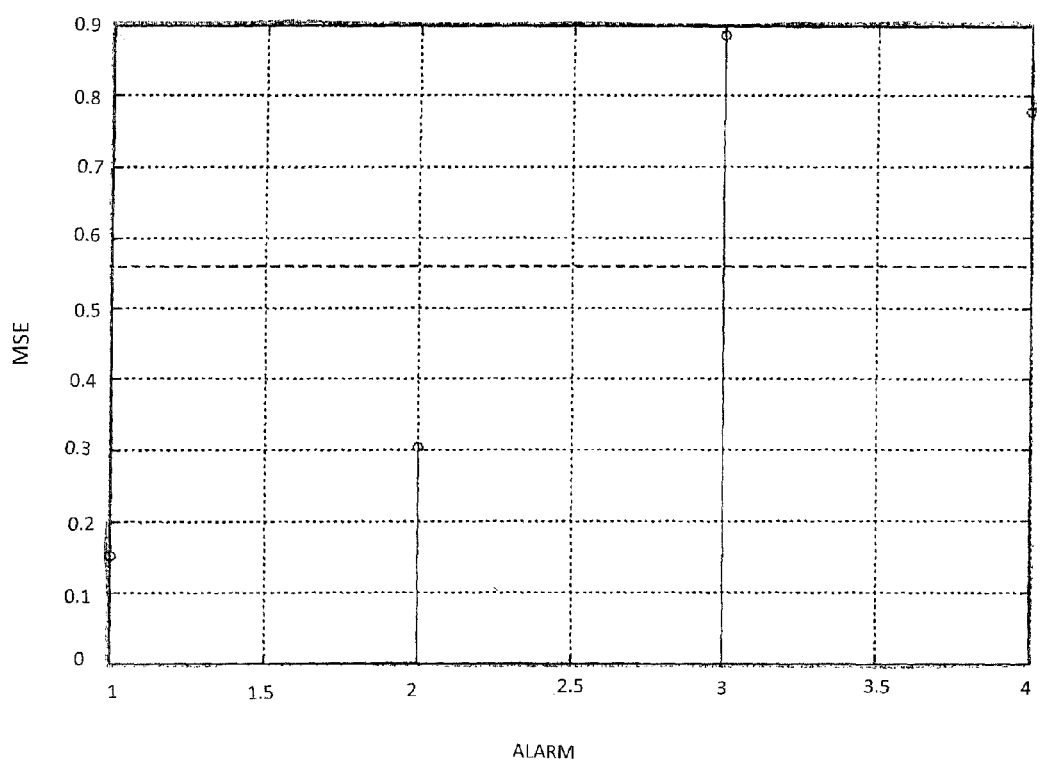
FIG. 3 is a graph showing the deviation away of local correlation vs. the global correlation when monitoring an Arterial blood pressure signal (ABP) for a patient with a clinical case of pulmonary edema.

FIG. 3 is a graph showing the deviation away of the local correlation vs. the global correlation when monitoring an Arterial blood pressure signal (ABP) for a patient with a clinical case of pulmonary edema. The first and second alarms have a low deviation away from the average deviation (the red dashed line), while the third and forth alarms have a significantly high deviation. This indicates that the first and second alarms are TRUE alarms while the third and fourth alarms are FALSE alarms.

While the preferred embodiments of the present invention have been illustrated and described, it will be understood by those skilled in the art that various changes and modifications may be made and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

What is claimed is:

1. A device comprising:
   a controller;
   a memory coupled to the controller; and
   an input interface which receives at least two event signals, wherein the controller determines:
      a global correlation matrix for the at least two event signals over a first period of time,
      a local correlation matrix for the at least two event signals over a second period of time which is shorter than the first period of time,
      a correlation vector indicative of a deviation between the local correlation matrix and the global correlation matrix,
      an average of the correlation vector, and
      whether an artifact was detected in one of the at least two event signals from the correlation vector and the average of the correlation vector.

2. The device according to claim 1 wherein said device is a patient monitoring system.

3. The device according to claim 2 wherein said at least two event signals are monitored patient data signals.

4. A patient monitoring system comprising:
   a controller;
   a memory coupled to the controller;
   an input interface configured to receive at least two event signals, the at least two event signals being patient monitored data signals;
   wherein the controller determines whether an artifact is detected by:
      repeatedly determining a global correlation for the at least two event signals over a first period of time,
      repeatedly determining a local correlation for the at least two event signals over a second period of time which is shorter than the first period of time,
      repeatedly determining a current deviation between the local correlation and the global correlation,
      determining an average deviation of a plurality of the current deviations, and
      determining whether an artifact was detected in one of the at least two event signals based on a difference between the current deviation and the average deviation; and
   an alarm indicator coupled to the controller, the alarm indicator being triggered if at least one of the event signals crosses a preset threshold value and the controller determines that no artifact was detected in the at least one event signal.

5. The device according to claim 1 further comprising a memory for recording the at least two event signals.

6. The device according to claim 1, wherein said device includes a server forming part of a client-server network.

7. A method for detecting a signal artifact in event signals, the method comprising the steps of:
   receiving at least two event signals;
   determining a global correlation for the at least two event signals over a first period of time;
   determining a local correlation for the at least two event signals over a second period of time which is shorter than the first period of time;
   repeatedly determining a current deviation between the local correlation and the global correlation;
   determining an average deviation from a plurality of the determined current deviations;
   comparing the current deviation and the average deviation to determine whether an artifact was detected in one of the at least two event signals; and
   triggering an alarm indication in response to determining that an artifact was detected.

8. The method according to claim 7 wherein said method is used with a patient monitoring system.

9. The method according to claim 8 wherein said at least two event signals are monitored patient data signals.

10. The method according to claim 9, said method further comprising the step of:
    providing the alarm indication in response to at least one of the event signals crossing a preset threshold value.

11. The method according to claim 7, said method further comprising the step of:
    recording the at least two event signals.

12. The method according to claim 7, wherein said method is used in a server forming part of a client-server network.

13. A system for detecting a signal artifact in an event signal, comprising:
    means for receiving at least two event signals;
    means for determining a global correlation for the at least two event signals over a first period of time;
    means for determining a local correlation for the at least two event signals over a second period of time which is shorter than the first period of time;
    means for determining a deviation between a local correlation vector and a global correlation vector;
    means for determining an average deviation from the deviation; and
    means for determining whether an artifact was detected in one of the at least two event signals based upon the average deviation.

14. The system according to claim 13 wherein said system is a patient monitoring system.

15. The system according to claim 14 wherein said at least two event signals are patient monitored data signals.

16. The system according to claim 13 further including:
    means for monitoring at least one physiological parameter of a patient and generating the at least two event signals, said at least two event signals conveying patient physiological parameter data.

* * * * *